(12) United States Patent
Rodriguez

(10) Patent No.: US 6,193,740 B1
(45) Date of Patent: Feb. 27, 2001

(54) EYE PILLOWS WITH ADJUSTABLE STRAP

(76) Inventor: Andrea Janine Rodriguez, 655 Edgewood Ave., Mill Valley, CA (US) 94941

( * ) Notice: Subject to any disclaimer, the term of this patent is extended or adjusted under 35 U.S.C. 154(b) by 0 days.

(21) Appl. No.: 09/216,360

(22) Filed: Dec. 18, 1998

Related U.S. Application Data

(60) Provisional application No. 60/068,266, filed on Dec. 19, 1997.

(51) Int. Cl.$^7$ ................................................ A61F 5/00
(52) U.S. Cl. ........................... 606/204.25; 606/204.15
(58) Field of Search .................. 2/13, 15; 128/858; 606/201, 204.25, 204.15, 204

(56) References Cited

U.S. PATENT DOCUMENTS

| | | | | |
|---|---|---|---|---|
| 1,924,315 | * | 8/1933 | Hemphill et al. | 2/15 |
| 2,537,768 | * | 1/1951 | Laporte | 2/15 |
| 2,891,252 | * | 6/1959 | Lazo | 2/15 |
| 2,942,270 | * | 6/1960 | Enright | 2/15 |
| 4,908,878 | * | 3/1990 | Tarragano | 2/15 |
| 5,343,561 | * | 9/1994 | Adamo | 2/15 |
| 5,389,066 | * | 2/1995 | Rhame | 128/858 |
| 5,700,238 | * | 12/1997 | Hyson | 602/74 |

* cited by examiner

*Primary Examiner*—Glenn K. Dawson
(74) *Attorney, Agent, or Firm*—Limbach & Limbach LLP

(57) ABSTRACT

The eye pillows of the present invention, used for therapeutic treatment of a user's eye and accu-pressure points around the user's eye, each include a hollow shell formed of a pliable material, and a predetermined amount of particulate material having a predetermined weight contained in the shell. The amount and weight of the particulate material and the pliability of the shell are selected so that when the pillow is placed over a user's eye, the shell conforms to, fills in, and applies evenly distributed pressure to the eye socket around the user's eye, including evenly distributed pressure to accu-pressure points around the eye. The pillows can be individually applied, connected together with a strap or head band, or even removably or integrally attached to a larger pillow or mask.

9 Claims, 5 Drawing Sheets

EYE PILLOWS WITH ADJUSTABLE STRAP

This application claims the benefit of U.S. Provision Application No. 60/068,266, filed Dec. 19, 1997, entitled "Eye Bags/Pillows with Adjustable Headstraps".

FIELD OF THE INVENTION

The present invention relates to eye pillows for soothing and treating the accu-pressure points around the eye, and more particularly to eye pillows that provide evenly distributed and adjustable pressure to the eyelid and eye socket area while providing full access to a user's face for bodywork and facial treatments without leveraged pressure over the nose, forehead and temple areas but with multifaceted interchangeable use.

BACKGROUND OF THE INVENTION

Many types of eye masks, pillows and compresses have been developed to cover a user's eyes to aid in sleeping as well as apply pressure on the user's face for therapeutic effect.

Eye masks were developed to keep light out while the user rested or slept. They are designed to be lightweight and non cumbersome. Due to their lightweight construction, a strap can effectively be used to keep them secure while the user sits or lies down.

Eye pillows were developed to block out light, but also provide additional therapeutic benefits. A single eye pillow is generally rectangular or oval in shape, much heavier than eye masks, and spans over and provides weighted coverage on the forehead, cheeks, eyes, nose and temple area.

Eye pillows can be made of a pliable material and filled with a particulate material such as flax seed. The pillows can be heated or cooled to provide the desired effect when laid across the user's face while the user is on their back. Due to their heavy weighted coverage, the user must remain in a stationary position on their back to prevent the pillow from falling off. Alternately, a head strap can be used to keep the pillow on the user in a sleeping or sitting position, but such a strap is largely unsuccessful. Herbal mixtures can be added to the pillows to provide aroma therapy for increased states of relaxation and pain relief. Eye pillows are generally used for short naps, relaxation times and during therapeutic bodywork sessions while the user lies stationary on their back. However, it must be removed when the therapist works on the user's face or turns the user on their side or stomach.

One drawback to conventional eye pillows is that they fail to provide even pressure distribution around the eye because they leave a gap around the eye socket thereby causing an unbalance feeling on the part of the user. Most of the pressure is applied on the forehead, nose bridge, cheeks and/or temples, with very little pressure applied inside the eye socket. There are a number of accu-pressure points that exist around the eye socket. It has been found that evenly distributed pressure applied to these accu-pressure points increases the beneficial treatments of eye strain, headaches, sinus problems, and cosmetic problems such as puffy eyes and dark circles. Such pressure also increases circulation and creates a soothing and comforting effect on the user. Evenly applied pressure on the eyelid itself can also be quite soothing as well as successfully alleviating certain types of headaches. These pressure points 1 around the eye socket 2 are illustrated in FIG. 1. An eye pillow draped across the face of a user fails to provide even pressure on the accu-pressure points around the eye socket. In fact, the accu-pressure points below the eyebrow and along the nose and inner eye are especially difficult to access because for most people, the eye socket is most recessed at those locations. Thus, a flat pillow design simply cannot rest on the user's forehead and nose while still applying even pressure to these hard to access accu-pressure points.

Shaped masks have been developed to block out light and some provide pressure in and around the eye. Such masks have been made out of foam, or even filled with a liquid gel that can be heated or cooled before use. These masks are shaped to fit around the nose to better access the eye socket. However, the problem with these shaped masks is that they still cannot provide sufficiently even pressure to all accu-pressure points around and on the eye for most users. The shape, size and depth of eye sockets, and the spacing between eye sockets, varies widely among different users. A generic shaped mask simply cannot reliably apply the desired evenly applied pressure to all the accu-pressure points for various users.

It is also desirable either during use, or from use to use, to vary the pressure distribution applied in the eye socket by the mask. However, shaped masks in general have a fixed shape that does not allow sufficient variations of pressure distributions by the user.

Eye pillows and shaped masks are often used by therapists during face massage and other body work to relax the patient. However, the therapists need to access the rest of the patient's face, when doing a facial massage, as well as move the patient during non-facial therapy. Sometimes the therapist needs to access the eye socket itself. Conventional eye pillows and masks block access to the patient's face, and tend to fall off or shift when the patient is moved. Therapists are forced to remove the pillows and masks in order to provide a comprehensive therapy session, which diminishes the relaxation effects of the treatment and can cause distress due to the rapid change of state. Straps used to hold the pillows and masks in place tend to uncomfortably exert pressure from the cheek bones all the way to the back of the head, including the temple area, further blocking a therapists' access to the patient's face and head areas. Tight head straps necessary to hold such pillows in place tend to be uncomfortable and hold the pillow too tightly onto the user's face.

There is a need for a eye pillow that evenly applies pressure on the accu-pressure points around the eye, and applies adjustable pressure on the eye itself, despite the different eye socket shapes and separations among various users. There is also a need for such an eye pillow to accommodate variations in the pressure distribution around the socket during use, to not exert pressure onto other parts of the user's head, to not block access to the user's face, to not require tight head straps to stay in place, and to provide multifaceted and interchangeable use for various therapeutic uses.

SUMMARY OF THE INVENTION

The present invention solves the aforementioned problems by providing pillows filled with particulate fill and made of such a pliable material to conform to and fill into a users's eye socket for evenly dispersed pressure over the eye lid and the pressure points adjacent thereto.

Specifically, the eye pillow of the present invention, used for therapeutic treatment of a user's eye and accu-pressure points around the user's eye, include a first pillow that has a first hollow shell formed of a pliable material, and a predetermined amount of particulate material having a predetermined weight and contained in the first shell. The amount and weight of the particulate material and the pliability of the first shell are selected so that when the first pillow is placed over a user's eye, the first shell conforms to, fills in, and applies evenly distributed pressure to the eye socket around the user's eye, including evenly distributed pressure to accupressure points around the eye.

Other objects and features of the present invention will become apparent by a review of the specification, claims and appended figures.

DETAILED DESCRIPTION OF THE PREFERRED EMBODIMENTS

The present invention is a pair of eye pillows that comfortably conform to, and exert evenly distributed and adjustable pressure to, the eye socket of a user.

Figure 1:
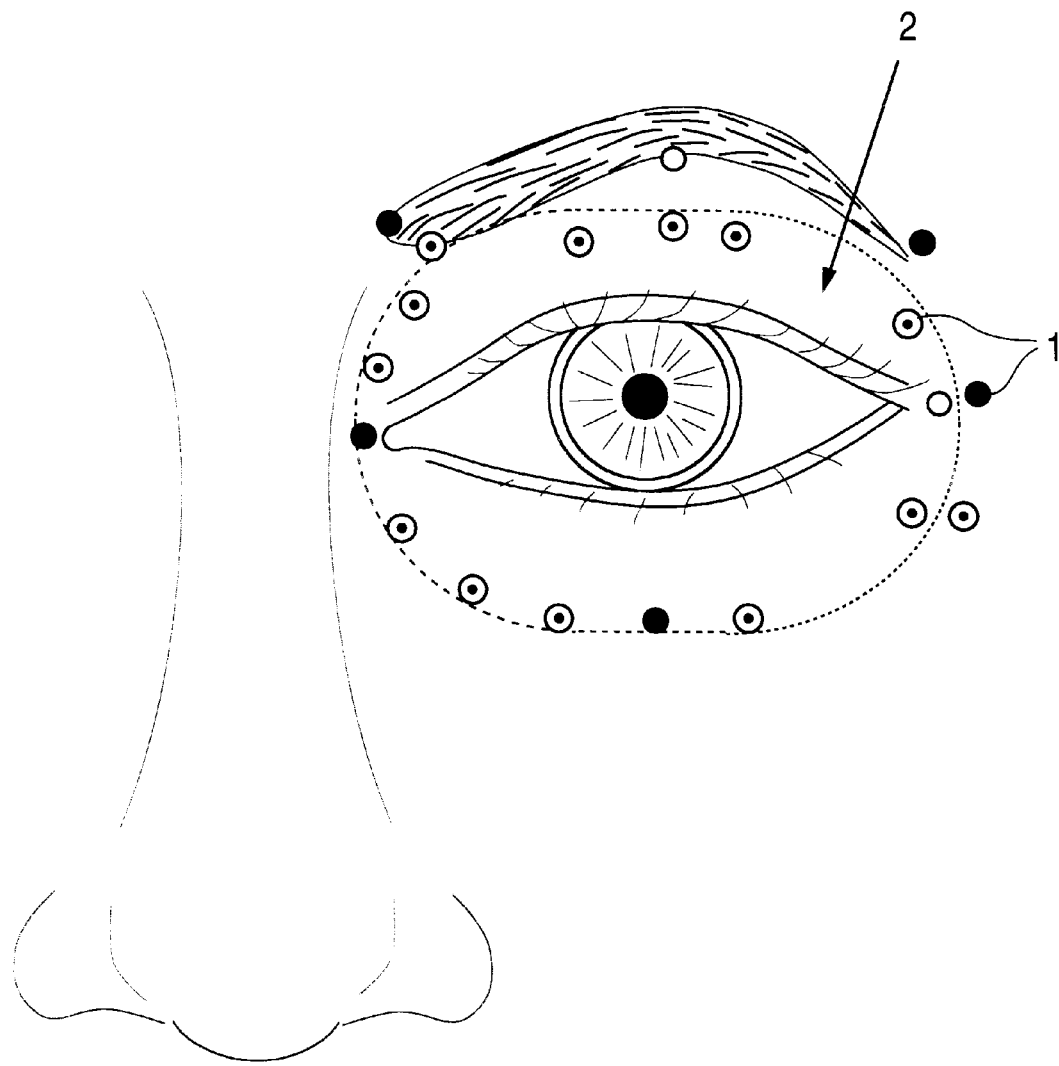
FIG. 1 is a front view of the accu-pressure points around a human eye.
Figure 2A:
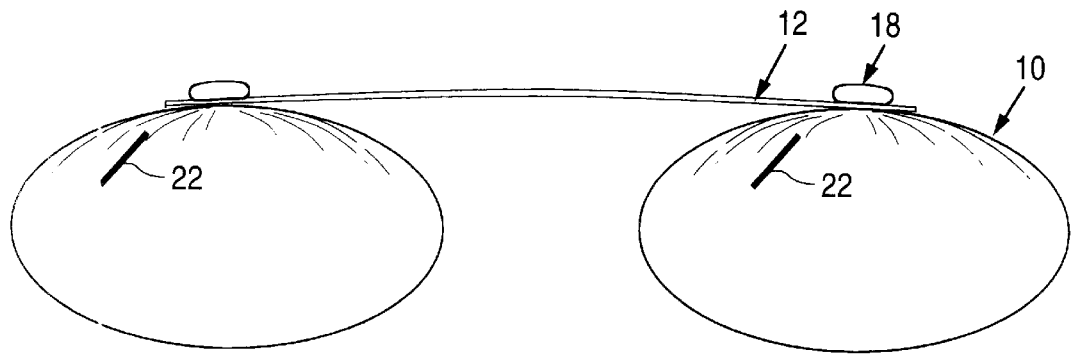
FIG. 2A is a side view of the eye pillows of the present invention.
Figure 2B:
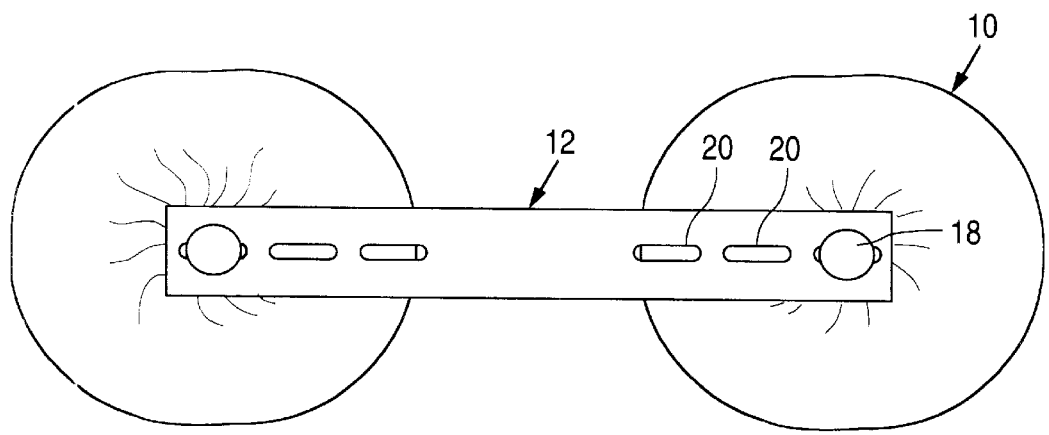
FIG. 2B is a top view of the eye pillows of the present invention.
Figure 2C:
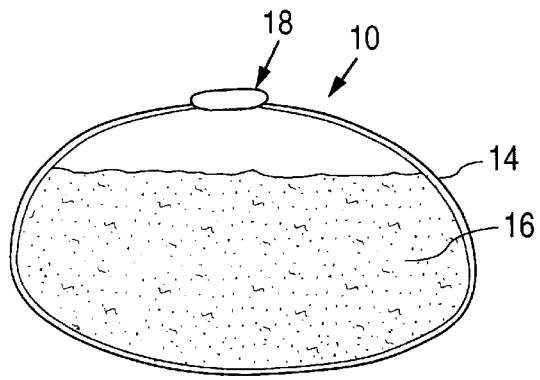
FIG. 2C is a side cross-sectional view of an eye pillow of the present invention.

The eye pillows 10 of the present invention are illustrated in FIGS. 2A–2B, and are removably attached to each other by a strap 12. The pillows 10 are made of a bag shaped shell 14 of pliable material, such as silk, and contain a particulate based fill 16 such as flax seed as illustrated in FIG. 2C.

Buttons 18 are attached to the top of the pillows 10 for engaging button holes 20 of strap 12. Closable access openings 22 can be formed in the shell 14 for adding or removing the amount of particulate fill 16 in pillows 10, or even removing all of the particulate fill 16 so pillows 10 can be washed. Openings 22 are preferably held closed with hook and fabric (Velcro™), a zipper, snaps, buttons, etc.

The size of each pillow 10, and the amount and weight of the particulate fill 16 therein, are selected so that when the pillow 10 is placed in an eye socket, it fully conforms to and fills into the eye socket by its own weight and pliability, thereby exerting even pressure throughout the eye socket (including on all the accu-pressure points and on the eye lid itself). The pillows 10 also block out all the incoming light.

Ideally, strap 12 loosely drapes over the user's nose during use while allowing the pillows 10 to be placed properly and fully conform into the eye socket. Separation between the pillows 10 is adjustable using buttons 18 and the various button holes 20. Since the pillows 10 fully conform into each eye socket, the eye sockets themselves hold the pillows 10 in place, thus allowing a user to move around a bit while on their back. A therapist can access all areas of the face and head, including working underneath the pillow and on the eye sockets (by lifting up on one edge of the pillow 10) without removing the pillow and disrupting the therapeutic effect thereof on the user. Prior art masks and pillows require removal in order to allow access to these areas.

Figure 3:
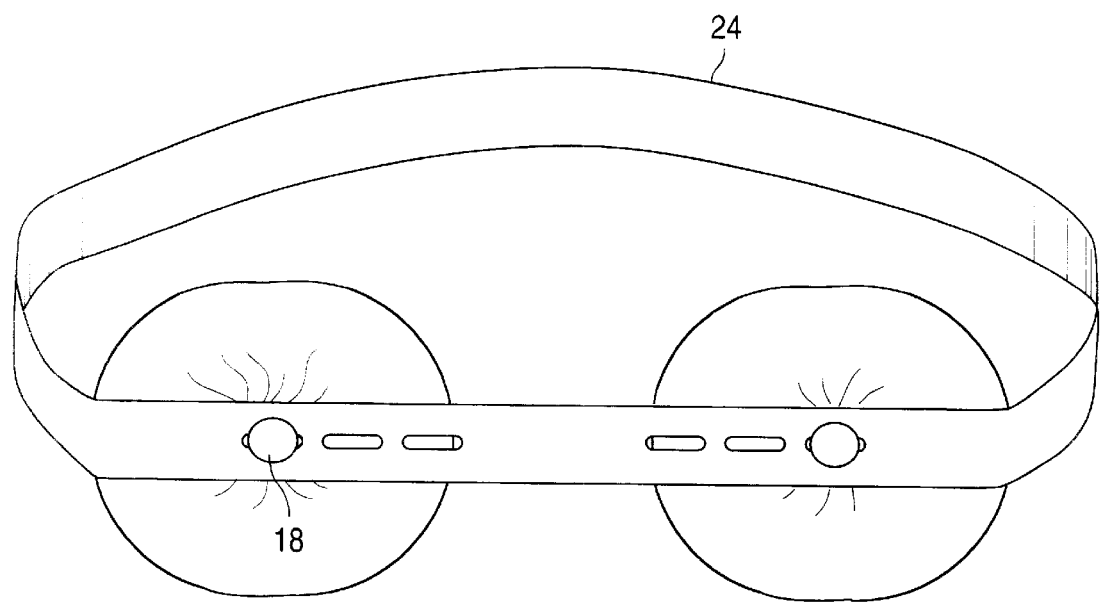
FIG. 3 is a perspective view of the pillows of the present invention attached to a head strap.

If the user does plan on using the pillows 10 while not lying on their back, then strap 12 can be replaced by a head strap 24, as illustrated in FIG. 3. Head strap 24 secures to the top elevated portion of eye pillows 10 (at buttons 18) and around the head, thus providing a space that does not contact the temple area. When the user wears the eye pillows 10 with the buttons 18 facing away from the eyes, head strap 24 will pass over, but not contact, with the temple areas of the user's head. This allows a therapist access to all areas of the face, including the temple area, without having to remove the eye pillows. It also allows the user to sit up or lie on their side or stomach while wearing pillows 10. Moreover, since the pillows 10 are conformed into the eye sockets, less pressure needs to be exerted by head strap 24 to maintain proper pillow position. Thus, tight uncomfortable head straps are avoided for better comfort.

Straps 12/24 can be removed altogether so that both pillows 10 can be worn without any straps, such as for sunbathing (no tan lines), facials, etc. Alternately, one of the pillows 10 can be used by itself. For example, if a user has an injury to a single eye which needs treatment, one of the pillows 10 can be removed from straps 12/24 and placed over that single eye. This individual pillow 10 can, with or without straps 12/24, also be used on the "third eye" accu-pressure point located between the eyebrows for meditation purposes.

Silk is preferably used for the shell 14. However, any material can be used for the material of shell 14 so long as it is pliable enough to allow pillow 10 to fully conform into the eye socket and is soothing to the eye. It is also preferable that the shell 14 sufficiently conduct heat into or out of pillow 10 for its cooling or heating effect, and/or allow any aroma of the particulate fill 16 to emanate therethrough. Examples of such materials include: cotton, rayon, polyester, hemp, velvet, terry cloth, Gortex™, gauze, spandex, thin rubber, latex, pliable plastic, cellophane, alathon, elastic, etc.

Particulate fill 16 is preferably flax seed, which has sufficient weight to conform pillow 10 to the eye socket while providing the necessary pressure distribution to all the accu-pressure points around the eye. Particulate fill has the additional advantage of allowing the user to manipulate pillow 10 to change the particulate distribution in pillow 10, thus changing the pressure distribution of pillow 10 onto the eye socket. It is preferable that the particulate fill 16 have thermal conductivity and heat capacity characteristics for temperature therapy (through shell 14) by providing a cooling or heating effect. For example, by placing the pillows 10 in a freezer before use, a cooling effect can be created. Alternately, by placing the pillows 10 in a microwave oven before use, a heating effect can be created.

The particulate fill 16 can further include herbal mixtures to provide aroma therapy for increased states of relaxation and pain relief. While flax seed is an ideal particulate fill, other particulate materials that can be used include beads, sand, herbs, grains, etc. It is important to loosely fill the pillow 10 with particulate fill 16. Overfilling or underfilling the pillow 10 will reduce the pillow's ability to conform to the users eye socket during use. The particulate fill 16 should fill up the pillow 10 between about one third full to about three quarters full to maintain adequate weight, mobility and adjustability of pillows 10. Straps 12 or 24 can be made of any of the materials used to make pillow 10, and additionally cording, string, and/or ribbon can be used.

While strap 12 is shown as being removably attached by buttons 18 to pillows 10, other attachment mechanisms could be used instead, such as hook and fabric (Velcro™), hook and eye, snaps, or even permanent stitching. In addition, removable and washable pillow cases can be attached around pillows 10 to keep them clean. These pillow cases can enclose around pillows 10 in a removable fashion, for example, by elastic strips, synch strings, etc., so the pillow cases can be removed and washed. Alternately, swatches of material can be placed over the eye socket before pillows 10 are inserted.

Figure 4:
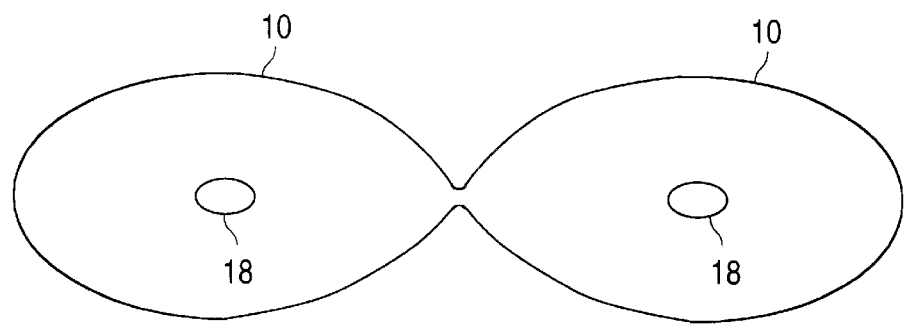
FIG. 4 is a side view of an alternate embodiment of the present invention.

FIG. 4 illustrates an alternate embodiment of the present invention, where a pair of pillows 10 are attached together, with no strap. The point at which the pillows are attached together could allow communication of particulate fill 16 from one pillow to travel to the other pillow to adjust the relative weight distribution between the two pillows.

Figure 5A:
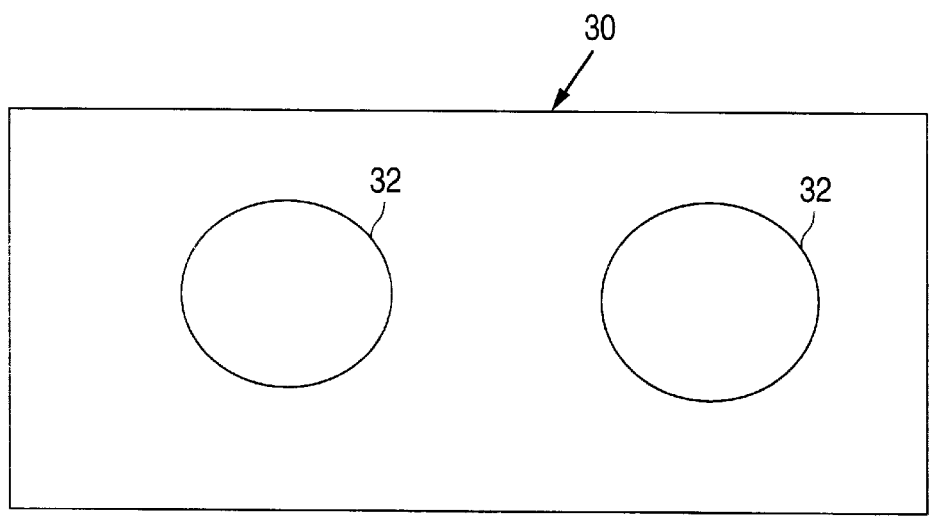
FIG. 5A is a top view of a second alternate embodiment of the present invention.
Figure 5B:
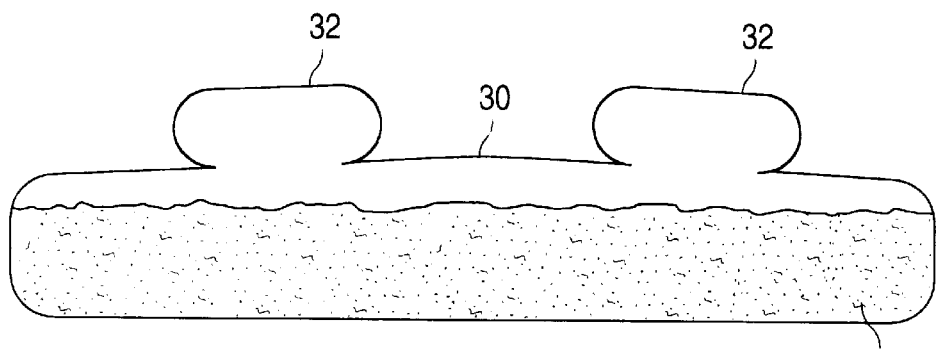
FIG. 5B is a cross-sectional side view of the second alternate embodiment of the present invention.
Figure 5C:
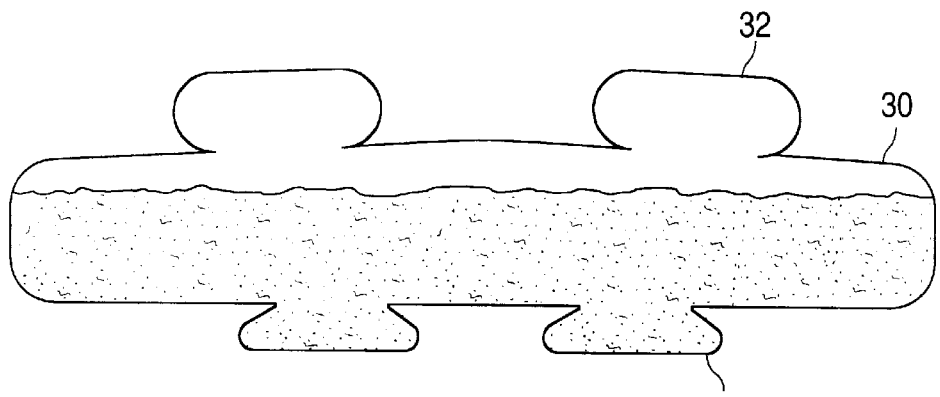
FIG. 5C is a cross-sectional side view of the second alternate embodiment of the present invention with a second set of pillows formed thereon.

FIGS. 5A–5B illustrates second alternate embodiment of the present invention. A large pillow 30 (for covering the user's face) is formed integrally with a pair of smaller eye pillows 32 (for filling in the eye sockets), so that particulate fill 16 therein freely flows between pillow 30 and pillows 32. This embodiment is ideal for therapy that calls for even pressure not only in the eye sockets, but also on parts of the face nearby the eye sockets. This embodiments allows the user to move the particulate fill 16 in pillow 30 and pillows 32 until there is the desired distribution of even pressure on the eye socket, nose, forehead, temple and/or cheeks. The heavier pillow 30 is held in place by pillows 32 conformed in and filled into the eye sockets. The back side of pillow 30 gives the user the versatility of using a flat pillow without any eye pillows extending therefrom. Additionally, a second pair of pillows 34 can be integrally formed into the opposite side of the pillow 30 as shown in FIG. 5C. The second pair of pillows 34 can have a different spacing and/or size for versatility.

Figure 6:
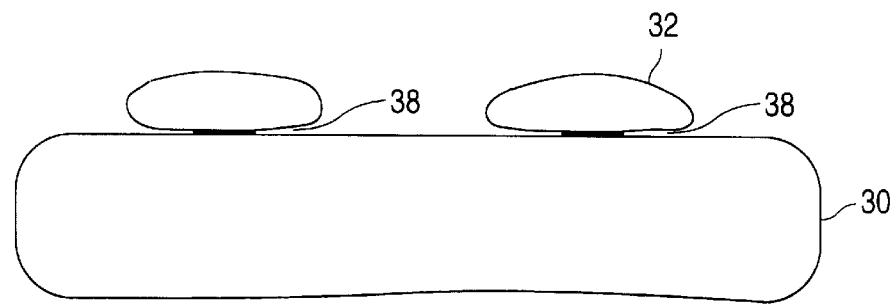
FIG. 6 is a side view of a third alternate embodiment of the present invention.

FIG. 6 illustrates a third alternate embodiment of the present invention, where the pillow 30 of FIGS. 5A and 5B is formed non-integrally with the pair of eye pillows 32, so the particulate fill 16 does not flow freely between the pillows 32 and pillow 30. This embodiment is ideal in that pillows 32 can be removably attached to pillow 30 (i.e. with Velcro™ pads 38) so that the separation of pillows 32 can be adjusted for proper fit, or pillows 32 can be removed altogether from pillow 30 and either used alone or with a strap as shown in FIGS. 2A–B or 3 for further versatility and multifaced use.

Figure 7:
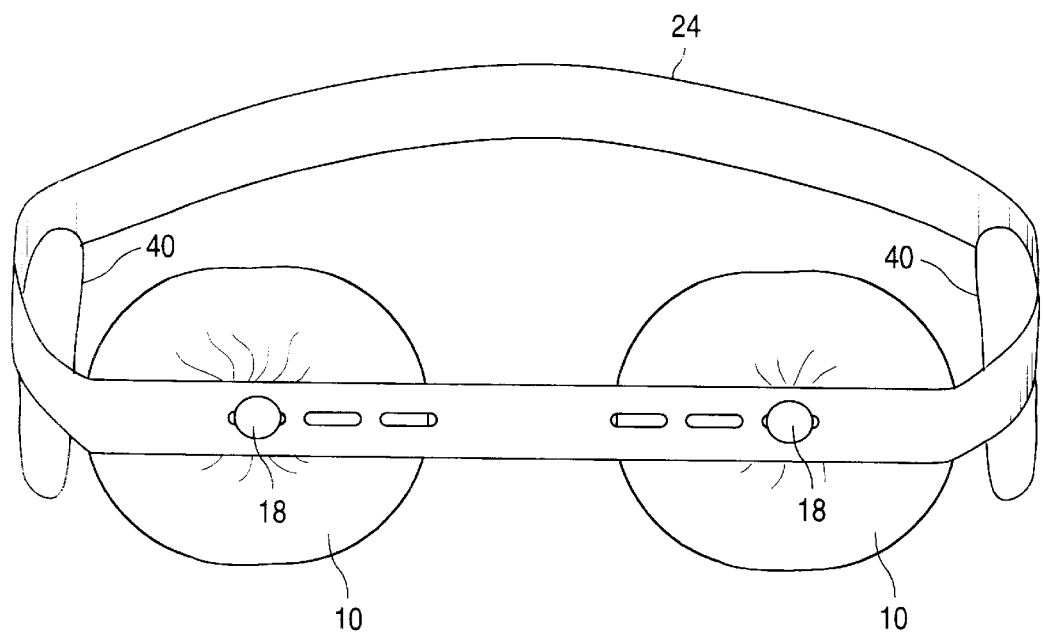
FIG. 7 is a perspective view of a fourth alternate embodiment of the present invention.

FIG. 7 illustrates a fourth alternate embodiment of the present invention, where temple pillows 40 are added to the inside of head strap 24 of the embodiment in FIG. 3, to apply soothing pressure and cooling/heating therapy to the temples of the user.

Figure 8:
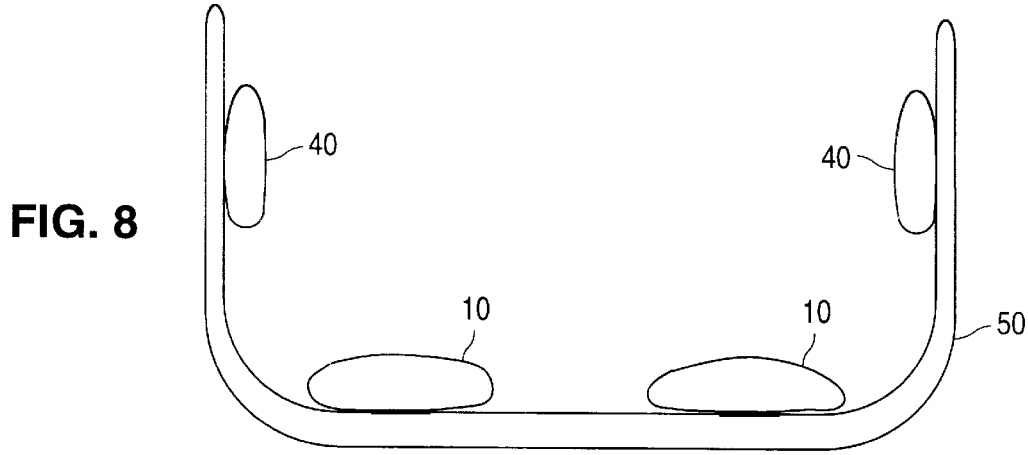
FIG. 8 is a top view of a fifth alternate embodiment of the present invention.

FIG. 8 illustrates a fifth alternate embodiment of the present invention, where pillows 10 and temple pillows 40 are attached to a head band 50. Head band 50 connects pillows 10 (which are conformed into the eye sockets) to temple pillows 40 (through which headband 50 exert pressure) to pillows 10 and 40 stay in place. Head band 50 is preferably made of plastic or metal wire.

Figure 9:
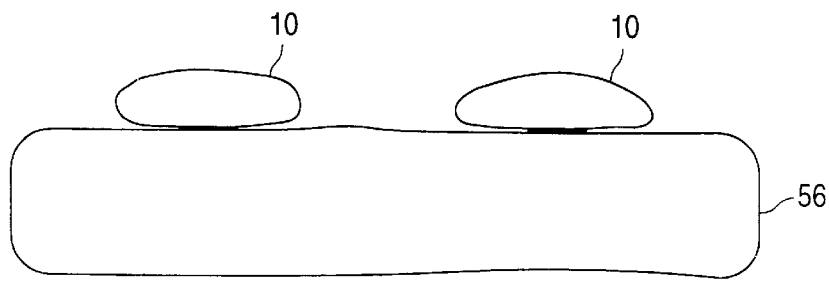
FIG. 9 is a side view of a sixth alternate embodiment of the present invention.

FIG. 9 illustrated a sixth alternate embodiment of the present invention, where pillows 10 are attached to a solid mask 56, which is constructed of cotton, foam or other comfortable and preferably compressible material.

It is to be understood that the present invention is not limited to the embodiments described above and illustrated herein, but encompasses any and all variations falling within the scope of the appended claims. For example, the pillows can be formed in any shape that fills the eye socket during use, including the following shapes: bag, cat-eye, rectangular, square, etc.

What is claimed is:

1. An eye pillow for therapeutic treatment of a user's eye, eye socket, and accu-pressure points around the user's eye, comprising:
  a first pillow that includes:
    a first hollow shell formed of a pliable material, and
    a predetermined amount of particulate material, having a predetermined weight, contained in the first shell,
    wherein the amount and weight of the particulate material and the pliability of the first shell are selected so that when the first pillow is placed over a user's eye, the first shell conforms to, fills in, and applies evenly distributed pressure to the eye socket around the user's eye, including evenly distributed pressure to accu-pressure points around the eye;
  a second pillow that includes:
    a second hollow shell formed of a pliable material,
    a predetermined amount of particulate material, having a predetermined weight, contained in the second shell,
    wherein the amount and weight of the particulate material and the pliability of the second shell are selected so that when the second pillow is placed over a user's eye, the second shell conforms to, fills in, and applies evenly distributed pressure to the eye socket around the user's eye, including evenly distributed pressure to accu-pressure points around the eye;

one of a strap and a head bandis-connected to the first and second shells; and a third pillow attached to the first and second pillows, the third pillow being larger than the first and second pillows.

2. An eye pillow for therapeutic treatment of a user's eye, eye socket, and accu-pressure points around the user's eye, comprising:

a first pillow that includes:
a first hollow shell formed of a pliable material, and
a predetermined amount of particulate material, having a predetermined weight, contained in the first shell,
wherein the amount and weight of the particulate material and the pliability of the first shell are selected so that when the first pillow is placed over a user's eye, the first shell conforms to, fills in, and applies evenly distributed pressure to the eye socket around the user's eye, including evenly distributed pressure to accu-pressure points around the eye;

a second pillow that includes:
a second hollow shell formed of a pliable material,
a predetermined amount of particulate material, having a predetermined weight, contained in the second shell, and
wherein the amount and weight of the particulate material and the pliability of the second shell are selected so that when the second pillow is placed over a user's eye, the second shell conforms to, fills in, and applies evenly distributed pressure to the eye socket around the user's eye, including evenly distributed pressure to accu-pressure points around the eye;

a third pillow that includes:
a third hollow shell formed of a pliable material,
particulate material contained in the third shell; and
wherein the first and second pillows are removably attached to the third shell.

3. An eye pillow for therapeutic treatment of a user's eye, eye socket, and accu-pressure points around the user's eye, comprising:

a first pillow that includes:
a first hollow shell formed of a pliable material, and
a predetermined amount of particulate material, having a predetermined weight, contained in the first shell,
wherein the amount and weight of the particulate material and the pliability of the first shell are selected so that when the first pillow is placed over a user's eye, the first shell conforms to, fills in, and applies evenly distributed pressure to the eye socket around the user's eye, including evenly distributed pressure to accu-pressure points around the eye;

a second pillow that includes:
a second hollow shell formed of a pliable material,
a predetermined amount of particulate material, having a predetermined weight, contained in the second shell, and
wherein the amount and weight of the particulate material and the pliability of the second shell are selected so that when the second pillow is placed over a user's eye, the second shell conforms to, fills in, and applies evenly distributed pressure to the eye socket around the user's eye, including evenly distributed pressure to accu-pressure points around the eye;

a third pillow that includes:
a third hollow shell formed of a pliable material,
particulate material contained in the third shell; and
wherein the first and second pillows are integrally formed with the third pillow so that the particulate material freely flows between the third shell and the first and second shells.

4. The eye pillow of claim 3, further comprising:

a fourth pillow that includes:
a fourth hollow shell formed of a pliable material,
a predetermined amount of particulate material, having a predetermined weight, contained in the fourth shell, and
wherein the amount and weight of the particulate material and the pliability of the fourth shell are selected so that when the fourth pillow is placed over a user's eye, the fourth shell conforms to, fills in, and applies evenly distributed pressure to the eye socket around the user's eye, including evenly distributed pressure to accu-pressure points around the eye;

a fifth pillow that includes:
a fifth hollow shell formed of a pliable material,
a predetermined amount of particulate material, having a predetermined weight, contained in the fifth shell, and
wherein the amount and weight of the particulate material and the pliability of the fifth shell are selected so that when the fifth pillow is placed over a user's eye, the fifth shell conforms to, fills in, and applies evenly distributed pressure to the eye socket around the user's eye, including evenly distributed pressure to accu-pressure points around the eye;
wherein the third shell has a front and a back surface, the first and second pillows are integrally formed with the front surface of the third shell so that the particulate material freely flows between the third shell and the first and second shells, and wherein the fourth and fifth pillows are integrally formed with the back surface of the third shell so that the particulate material freely flows between the third shell and the fourth and fifth shells.

5. The eye pillow of claim 4, wherein the third pillow is significantly larger than the first and second pillows.

6. The eye pillow of claim 4, wherein the first and second pillows are spaced apart a distance that is different from a spacing between the fourth and fifth pillows.

7. The eye pillow of claim 6, wherein the first and second pillows have a different size than the fourth and fifth pillows.

8. An eye pillow for therapeutic treatment of a user's eye, eye socket, temple and accu-pressure points around the user's eye, comprising:

a first pillow that includes:
a first hollow shell formed of a pliable material, and
a predetermined amount of particulate material, having a predetermined weight, contained in the first shell,
wherein the amount and weight of the particulate material and the pliability of the first shell are selected so that when the first pillow is placed over a user's eye, the first shell conforms to, fills in, and applies evenly distributed pressure to the eye socket around the user's eye, including evenly distributed pressure to accu-pressure points around the eye;

a second pillow that includes:
   a second hollow shell formed of a pliable material,
   a predetermined amount of particulate material, having a predetermined weight, contained in the second shell,
   wherein the amount and weight of the particulate material and the pliability of the second shell are selected so that when the second pillow is placed over a user's eye, the second shell conforms to, fills in, and applies evenly distributed pressure to the eye socket around the user's eye, including evenly distributed pressure to accu-pressure points around the eye;

one of a strap and a head band is connected to the first and second shells; and at least one additional pillow that includes:
   an additional hollow shell formed of a pliable material,
   a predetermined amount of particulate material, having a predetermined weight, contained in the addition shell,
   wherein the one strap and head band supporting the first and second pillows over the user's eyes, and supporting the additional pillow over the user's temple.

9. An eye pillow for therapeutic treatment of a user's eye, eye socket, and accu-pressure points around the user's eye, comprising:

a first pillow that includes:
   a first hollow shell formed of a pliable material, and
   a predetermined amount of particulate material, having a predetermined weight, contained in the first shell,
   wherein the amount and weight of the particulate material and the pliability of the first shell are selected so that when the first pillow is placed over a user's eye, the first shell conforms to, fills in, and applies evenly distributed pressure to the eye socket around the user's eye, including evenly distributed pressure to accu-pressure points around the eye;

a second pillow that includes:
   a second hollow shell formed of a pliable material, and
   a predetermined amount of particulate material, having a predetermined weight, contained in the second shell;
   wherein the amount and weight of the particulate material and the pliability of the second shell are selected so that when the second pillow is placed over a user's eye, the second shell conforms to, fills in, and applies evenly distributed pressure to the eye socket around the user's eye, including evenly distributed pressure to accu-pressure points around the eye, and wherein the first and second pillows are integrally formed with each other so that the particulate material freely flows between the first and second shells.

\* \* \* \* \*